US005835230A

United States Patent [19]
McAndrew et al.

[11] Patent Number: 5,835,230
[45] Date of Patent: Nov. 10, 1998

[54] METHOD FOR CALIBRATION OF A SPECTROSCOPIC SENSOR

[75] Inventors: James J. F. McAndrew, Lockport; Ronald S. Inman, Lyons, both of Ill.

[73] Assignee: American Air Liquide Inc., Walnut Creek, Calif.

[21] Appl. No.: 890,926

[22] Filed: Jul. 10, 1997

[51] Int. Cl.$^6$ .......................... G01N 21/31; G01N 21/59
[52] U.S. Cl. ................................ 356/437; 250/252.1 A; 250/341.5; 356/439
[58] Field of Search ..................................... 356/437, 438, 356/439; 250/252.1 A, 339.09, 341.5

[56] References Cited

U.S. PATENT DOCUMENTS

| | | |
|---|---|---|
| 3,524,066 | 8/1970 | Blakkan . |
| 4,934,816 | 6/1990 | Silver et al. .............................. 356/409 |
| 4,937,461 | 6/1990 | Traina ...................................... 250/575 |
| 5,065,025 | 11/1991 | Doyle ....................................... 250/573 |
| 5,173,749 | 12/1992 | Tell et al. ................................. 356/437 |
| 5,352,902 | 10/1994 | Aoki ........................................ 250/575 |
| 5,485,276 | 1/1996 | Bien et al. ................................ 356/437 |
| 5,578,829 | 11/1996 | Talasek et al. . |

FOREIGN PATENT DOCUMENTS

| | | |
|---|---|---|
| 0015170 | 9/1980 | European Pat. Off. . |
| 0647845 | 4/1995 | European Pat. Off. . |
| 0 706 042 | 4/1996 | European Pat. Off. . |
| 3633931 | 4/1988 | Germany . |
| 4214840 | 11/1993 | Germany . |
| 2075213 | 11/1981 | United Kingdom . |
| 2165640 | 4/1986 | United Kingdom . |
| WO90/00732 | 1/1990 | WIPO . |

OTHER PUBLICATIONS

White, "Long Optical Paths of Large Aperture," J. Opt. Soc. Am., vol. 32 (1942), pp. 285–288.

T.A. Hu et al, "Improved Multipass Optics for Diode Laser Spectroscopy," Review of Scientific Instruments, vol. 64, No. 12, Dec. 1993, pp. 3380–3383).

Patent Abstracts of Japan, vol. 6, No. 59, JP 57–1953, Jan. 1982.

Fried et al, "Versatile Integrated Tunable Diode Laser System for High Precision: Application for Ambient Measurements of OCS," Applied Optics, vol. 30, No. 15, May 20, 1991, pp. 1916–1932.

May, "Correlation–Based Technique for Automated Tunable Diode Laser Scan Stabilization," Rev. Sci. Instrum, vol. 63, No. 5, May 1992, pp. 2922–2926.

Eng et al., "Tunable Diode Laser Spectroscopy: An Invited Review," Optical Engineering, Nov./Dec. 1980, vol. 19, No. 6, pp. 945–960.

(List continued on next page.)

*Primary Examiner*—Vincent P. McGraw
*Attorney, Agent, or Firm*—Burns, Doane, Swecker and Mathis, L.L.P.

[57] ABSTRACT

A novel method for calibration of a spectroscopic sensor is provided. In the method, a spectroscopic system is provided. The system includes a measurement cell having one or more walls which at least partially enclose a sample region. The cell further includes a light entry port and a light exit port. The light entry port and the light exit port can be the same port or separate ports. Each of the ports contains a light transmissive window through which a light beam passes along an internal light path inside the measurement cell. The system further has an optical chamber which contains a light source for generating the light beam which passes through the light entry port into the cell, and a detector for measuring the light beam exiting the cell through the light exit port. The light beam passes along an external light path inside the optical chamber. In addition, a gas inlet is connected to the optical chamber. A calibration gas stream is introduced into the optical chamber. The calibration gas stream contains a calibrating gas species and a carrier gas. The calibrating gas species is present in the calibration gas stream in a known concentration. A spectroscopy measurement of the calibration gas stream is then performed. The method finds particular applicability in the calibration of an in-line spectroscopic sensor useful in the detection of molecules of interest in a semiconductor processing tool.

9 Claims, 2 Drawing Sheets

OTHER PUBLICATIONS

Lundqvist et al, "Measurements of Pressure–Broadening Coefficients of NO and $O_3$ Using a Computerized Tunable Diode Laser Spectrometer," Applied Optics, vol. 21, No. 17, Sep. 1, 1982, pp. 3109–3113.

Ahlberg et al, "IR–Laser Spectroscopy for Measurement Applications in the Industrial Environment," TR 85170, Dec. 85.

Höjer et al, "Measurements of Electric Field Strength in Gas Insulated High–Voltage Components Using Infrared Diode Laser Absorption Spectroscopy," Applied Optics, vol. 25, No. 17, Sep. 1, 1986; pp. 2984–2987.

Cassidy, "Trace Gas Detection Using 1.3 $\mu$m InGaAsP Diode Laser Transmitter Modules," Applied Optics, vol. 27, No. 3, Feb. 1, 1988, pp. 610–614.

Mitsui et al, "Development of New APIMS for the Detection of Trace Impurities in Special Gases," Proceedings of the 40th Annual Technical Meeting of the IES, Chicago, pp. 246–253 (1994).

Herriott et al, "Folded Optical Delay Lines," Applied Optics, vol. 4, No. 8, pp. 883–889 (Aug. 1965).

METHOD FOR CALIBRATION OF A SPECTROSCOPIC SENSOR

BACKGROUND OF THE INVENTION

1. Field of the Invention

The present invention relates to a novel method for calibration of a spectroscopic sensor. The method finds particular applicability in the calibration of an in-line spectroscopic sensor which can be used in the detecting and measurement of gas phase species in a semiconductor processing tool.

2. Description of the Related Art

Spectroscopic sensors have found wide use in the detection of gas phase molecular species in gas samples. Examples of spectroscopic techniques which are applicable to such measurements include, for example, tunable diode laser absorption spectroscopy (TDLAS).

In absorption spectrometer systems, a light source is tuned to emit light at a particular wavelength which corresponds to a characteristic of the molecular species desired to be detected. The light beam generated by the light source is transmitted into a sample region within a measurement cell which contains the gas sample, i.e., the analyte, being measured.

The light source and detector are housed in an optical chamber, which is separated from the measurement cell by a light transmissive window. The light beam follows a path from the light source through the same or a different light transmissive window and into the sample region in the measurement cell. From the sample region, the beam exits the measurement cell by again passing through the same or different light transmissive window and into the optical chamber. Thus, the beam travels along a path within the optical chamber, i.e., the external light path, and along a path within the measurement cell, i.e., the internal light path.

The fraction of the light emitted by the light source which is transmitted through the sample is measured by the detector, with the intensity of light reaching the detector being determined by Beer's Law as follows:

$$I = I_o \cdot e^{-\alpha l c P}$$

where $I_o$ is the intensity of the incident radiation, $\alpha$ is the absorptivity, $l$ is the path length through the sample, $c$ is the concentration of the impurity in the sample (by volume), and $P$ is the total pressure of the sample.

For small absorptions, the amount of light absorbed is given by the equation:

$$I - I_o = \alpha l c P.$$

Based on the above equations, the extent of absorption is fully predictable for a wide range of wavelengths, pressures, temperatures and optical paths, provided certain key parameters are known, such as the incident light intensity, the absorption wavelength, the absorption coefficient, the temperature dependence of the absorption coefficient and the pressure broadening coefficient. Once the absorption is determined, the concentration of the molecular species of interest can be calculated. However, before such sensors can be used to provide accurate concentration measurements, calibration of the sensor is required to correlate the measured absorption signal with a concentration.

The most fundamental and widely used approach to the calibration of gas analysis equipment is the use of a calibration gas containing a known concentration of the species of interest. For example, in absorption spectroscopy, calibration is typically accomplished by introducing a known quantity of the molecule of interest into the measurement cell.

While such an approach can be used advantageously with certain sensor configurations, it cannot be used effectively with an in-situ (i.e., in-line) spectroscopic sensor. In-situ sensors are described by the present inventors in copending application Ser. No. 08/711,504, Attorney Docket No. 016499-204, filed Sep. 10, 1996, and in copending application Ser. No. 08/890,928, Attorney Docket No. 016499-373, filed on even date herewith, the contents of which applications are herein incorporated by reference.

As described in the aforementioned documents, a spectroscopic system can be used in conjunction with a processing apparatus, such as a semiconductor processing tool. As a result, in-situ spectroscopic measurements can be made inside the processing chamber or the chamber's exhaust line. Real-time measurements of the impurities of interest inside the processing tool can thereby be obtained.

Such in-situ measurement systems do not lend themselves to the conventional calibration approach described above. In particular, the species being introduced into the process chamber for calibration can be harmful to the process being run as well as to the semiconductor devices being fabricated. For example, moisture (under vapor) can cause corrosion of the devices being formed and can interfere with the chemistry of the process. Moreover, since moisture is difficult to remove from the process chamber due to its low pumping speed, the time to reach base pressure prior to processing can be significantly lengthened. In addition, the introduction of the calibration gas into the sample area via the processing tool can be a complicated task.

In another known method for calibrating spectroscopic sensors, use is made of a calibration cell which is distinct from the measurement cell. The calibration cell contains a known quantity of the species of interest, and is moved into the external light path during calibration and is removed from the external light path when performing actual measurements with the measurement cell. Although the optical path, pressure, concentration and other parameters of the calibration cell are often different from those in the measurement cell, the system can be calibrated once the relationships between the parameters of the two cells are known.

Use of a calibration cell in this manner is advantageous in that it allows for calibration without the introduction of potentially contaminating species into the measurement cell and processing tool. In addition, the calibration cell can be permanently sealed with a sample of the calibration gas inside, thereby reducing complications due to material handling.

While the calibration cell does provide a partial solution to the problems associated with direct injection of the calibration gas into the measurement cell, the calibration cell must be removed from the optical path when the measurement cell is in use. Thus, during operation of the measurement cell, it becomes necessary to move the calibration cell into and out of the external light path in the optical chamber.

In such a case, the optical path can be purged with an inert gas to prevent or minimize light absorption by atmospheric contaminants, such as water vapor. As a result, the spectroscopic system requires a relatively complicated mechanical system which can move the calibration cell into and out of the light path inside the purged optical chamber.

If the molecule of interest is water vapor or some other species which interacts strongly with the surfaces of the calibration cell, a continuous flow of gas containing a known concentration of the molecule of interest should be maintained through the calibration cell. This complicates matters still further.

Since in-line sensors cannot easily be calibrated by the above-described methods, the sensor is typically dismounted from the exhaust line or process chamber to which it is attached, and a known concentration of the molecule of interest is introduced into the sample region. Such dismantling of the sensor is not desired, since it may require that the process tool be shut down for extended periods of time.

To overcome the disadvantages associated with the related art, it is an object of the present invention to provide a novel method for calibrating a spectroscopic sensor. The method allows for accurate calibration of an absorption spectrometer which can be used to measure the concentration of gas phase molecular species in a sample. The inventive method can be performed in a far simpler manner than was previously possible. Particular applicability for the method is found in the calibration of an in-line spectroscopic sensor used in conjunction with a semiconductor processing tool.

Other objects and aspects of the present invention will become apparent to one of ordinary skill in the art on a review of the specification, drawings and claims appended hereto.

SUMMARY OF THE INVENTION

According to a first aspect of the present invention, a novel method for calibration of a spectroscopic sensor is provided. In the method, a spectroscopic system is provided. The system includes a measurement cell having one or more walls which at least partially enclose a sample region. The cell further includes a light entry port and a light exit port. The light entry port and the light exit port can be the same port or separate ports. Each of the ports contains a light transmissive window through which a light beam passes along an internal light path inside the measurement cell.

The system further has an optical chamber which contains a light source for generating the light beam which passes through the light entry port into the cell, and a detector for measuring the light beam exiting the cell through the light exit port. The light beam passes along an external light path inside the optical chamber. In addition, a gas inlet is connected to the optical chamber.

A calibration gas stream is introduced into the optical chamber. The calibration gas stream contains a calibrating gas species and a carrier gas. The calibrating gas species is present in the calibration gas stream in a known concentration. A spectroscopy measurement of the calibration gas stream is then performed.

According to a further aspect of the invention, the above-described method is used in the calibration of an in-line spectroscopic sensor.

According to yet another aspect of the invention, the method is used in the calibration of an in-line spectroscopic sensor in a semiconductor processing tool.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Through the invention, it has been recognized that the primary sources of deviation in performance of many spectroscopic sensors are drifts in the sensor system control electronics and in the properties of the light source and detector. Drifts in the detection electronics, while usually not large, are difficult to detect independently and have therefore been found to be of major importance in the calibration method according to the invention.

It has also been recognized that drifts in optical alignment, deterioration of optical properties of light transmissive windows and mirrors, and variations in detector response can be taken into account in the present method by measuring the total light intensity at the detector. These factors, therefore, are automatically taken into account by the inventive calibration method.

With the above in mind, the method according to the invention can be used to calibrate any spectroscopy measurement system which includes a measurement cell having an internal light path therein and an optical chamber which contains a light generation system, a light detection system and an external light path. Suitable systems include, for example, tunable diode laser absorption spectroscopy (TDLAS) systems.

Figure 1:
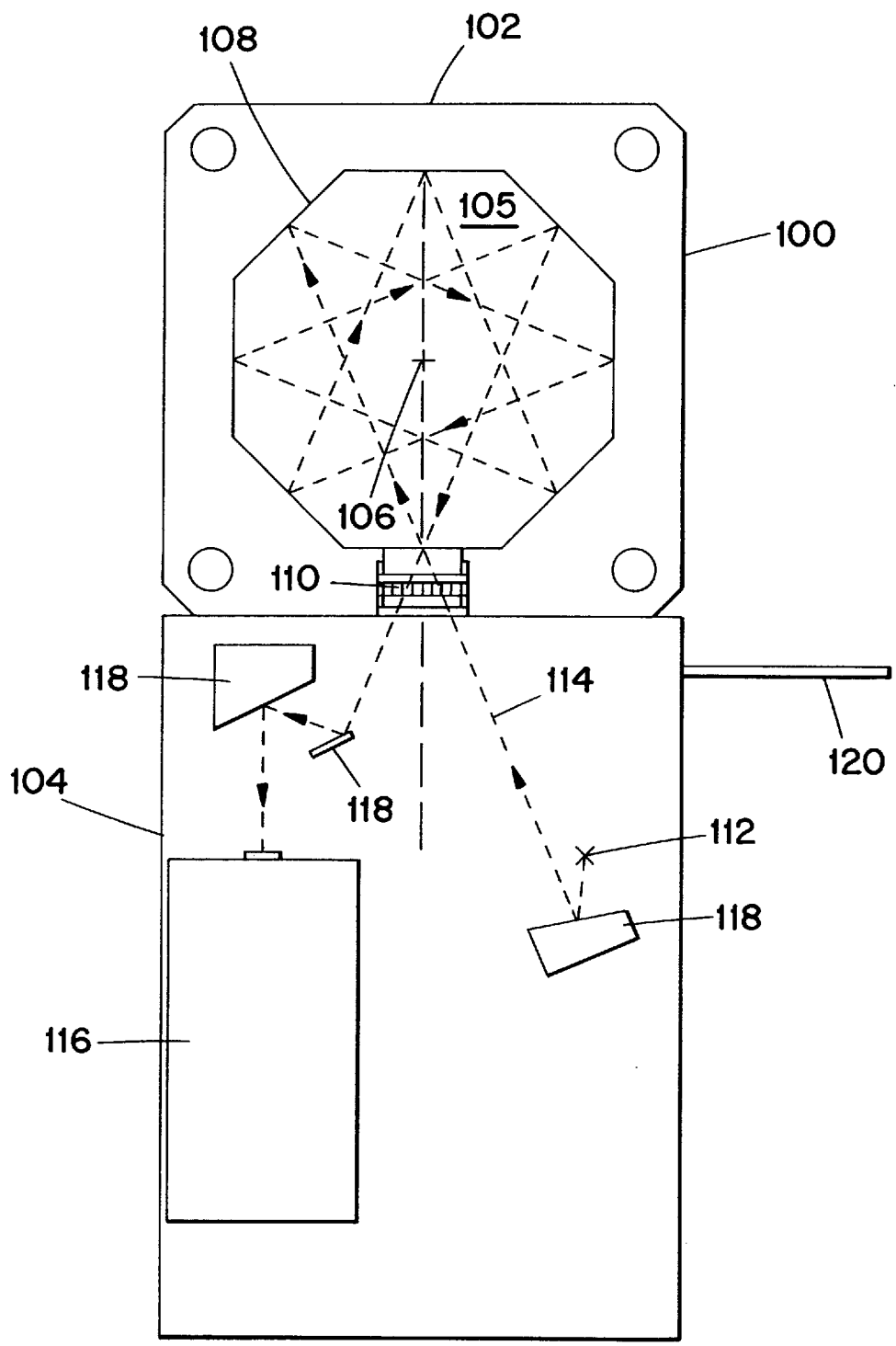
FIG. 1 is an in-line absorption spectroscopy measurement system which can be used to practice the present invention.

An exemplary TDLAS sensor system upon which the inventive method can be practiced is illustrated in FIG. 1. Sensor 100 is comprised of an in-line measurement cell 102 and an optical chamber 104. The measurement cell includes a sample region 105 circumscribed by a plurality of walls 108, each of which has a light reflective surface facing the sample region.

At least one side of the measurement cell has a light entry port 110 therein for allowing a light beam to pass from the optical chamber into the cell. In addition, one or more light exit ports 110 are provided for allowing the light beam to exit the cell. The light entry and exit ports can be the same port or different ports, with each port having a light transmissive window therein.

A light beam is directed through the light transmissive window into the cell to the sample region and out of the cell through the light transmissive window. While the extent of reflection of the light beam (if any) will vary depending on the type of measurement cell employed, light beam 106 in the exemplary cell is reflected from each wall at least once prior to exiting the cell through the entry/exit port.

Inside optical chamber 104, light source 112 is provided for generating the light beam 114. To measure the absorption of the light beam which exits the measurement cell, the system further includes a detector 116, which can be a photodiode. The system can further include ancillary optics, such as one or more mirrors 118 for guiding the light beam into the cell and/or to the detector, as well as control and signal processing electronics.

The light beam travels along an internal light path inside measurement cell 102, and along an external light path inside optical chamber 104. Thus, as used herein, the term "internal light path" refers to the path taken by the light beam within the measurement cell, while the term "external light path" refers to the path taken by the light beam within the optical chamber.

The optical chamber further includes a gas inlet 120, which is used to introduce a calibration gas stream into the optical chamber during calibration of the sensor. During normal operation of sensor system, a dry inert gas, such as nitrogen, helium or argon, can be introduced into the optical chamber to minimize any absorption loss due to atmospheric contaminants.

In accordance with the invention, the calibration gas stream contains a calibrating gas species and a carrier gas, with the calibrating gas species being at a known concentration. The calibrating gas species is preferably identical to the species desired to be measured. However, when the species of interest is toxic or when use of that species is otherwise not desirable, the system can be calibrated by introducing a substitute species (e.g., a non-toxic species) which absorbs light at a wavelength neighboring that of the species of interest. For example, in the case of the measurement of HF, it is possible to substitute therefor $H_2O$ as the calibrating gas species.

In the case of a spectroscopic system having an existing means for purging the external optical chamber, the species of interest can be introduced into the purge gas stream in a controlled fashion, such that the concentration of that species in the optical chamber can be well controlled. The inert purge gases described above will function well as the carrier gas in the calibration gas. The calibration gas is introduced into the optical chamber with a continuous flow.

The pressure inside the cell can be controlled automatically by normal leakage from the chamber. However, an exhaust line can optionally be connected to the optical chamber if more accurate pressure control in the cell is desired. Furthermore, in the case that toxic species are to be calibrated, the chamber can be air-tight, with an exhaust line connected thereto.

To provide a calibration gas of known concentration, the calibration species can be introduced into the purge gas line using a known permeation device. Alternatively, the calibration gas can be prepared geometrically in a cylinder, with the contents of the cylinder being used in lieu of the purge gas. The calibration gas can also be prepared by other known techniques for mixing gases using conventional gas flow control devices, such as mass flow controllers and valves. One method for providing such a flow is described in U.S. Pat. No. 4,849,174, the contents of which are herein incorporated by reference.

After initiation of the flow of the calibration gas into the optical chamber, a spectroscopy measurement is performed. The calibration gas flow results in a measurable signal, which once measured, provides a value which can be correlated to later spectroscopic measurements performed in the measurement cell.

The signal attributed to absorption can be affected by various non-absorption phenomena. For example, light scattering within the measurement cell, drifts in optical alignment, deterioration of optical properties of light transmissive windows and mirrors and variations in detector response can all affect the absorption signal. Because absorption and scattering inside the measurement cell are measured during the calibration measurement, the non-absorption related effects are automatically taken into account, resulting in highly accurate calibrations.

Thus, provided the relationship between the external light path and the internal light path remains substantially constant, the concentration in the exhaust line can be calculated once the concentration in the optical chamber is known. As used herein, the term "substantially constant" means within about 1%.

The easiest and most accurate way to determine the relationship between the light path in the measurement cell and in the optical chamber is by determining the concentration of a molecular species (e.g., water vapor, methane or carbon dioxide) which, when introduced into the optical chamber, provides the same absorption signal as a given, known concentration of that species in the measurement cell. Determination of the relationship between the two light paths can be accomplished by adjusting one or the other of the concentration in the optical chamber and the concentration in the measurement cell until the same absorption signal is obtained. This determination need only be made once, and would preferably be made at initial calibration of the sensor, prior to installation on the processing tool.

The calibration method in accordance with the invention is particularly versatile, in that the method can be performed when the sensor system is installed in the processing tool, or alternatively, while the sensor system is separated from the processing tool. The former case is preferred since, in the latter case, the sensor may become unavailable for use during semiconductor processing for extended periods of time.

The spectroscopic measurement for purposes of the invention can be performed with the measurement cell being under vacuum or, alternatively, with the measurement cell being purged with a pure gas, such as nitrogen, helium or argon. When calibration is to be carried out with the measurement cell installed in a semiconductor processing tool, a vacuum in the measurement cell can conveniently be applied, since such processing tools are generally vacuum processes.

Figure 2:
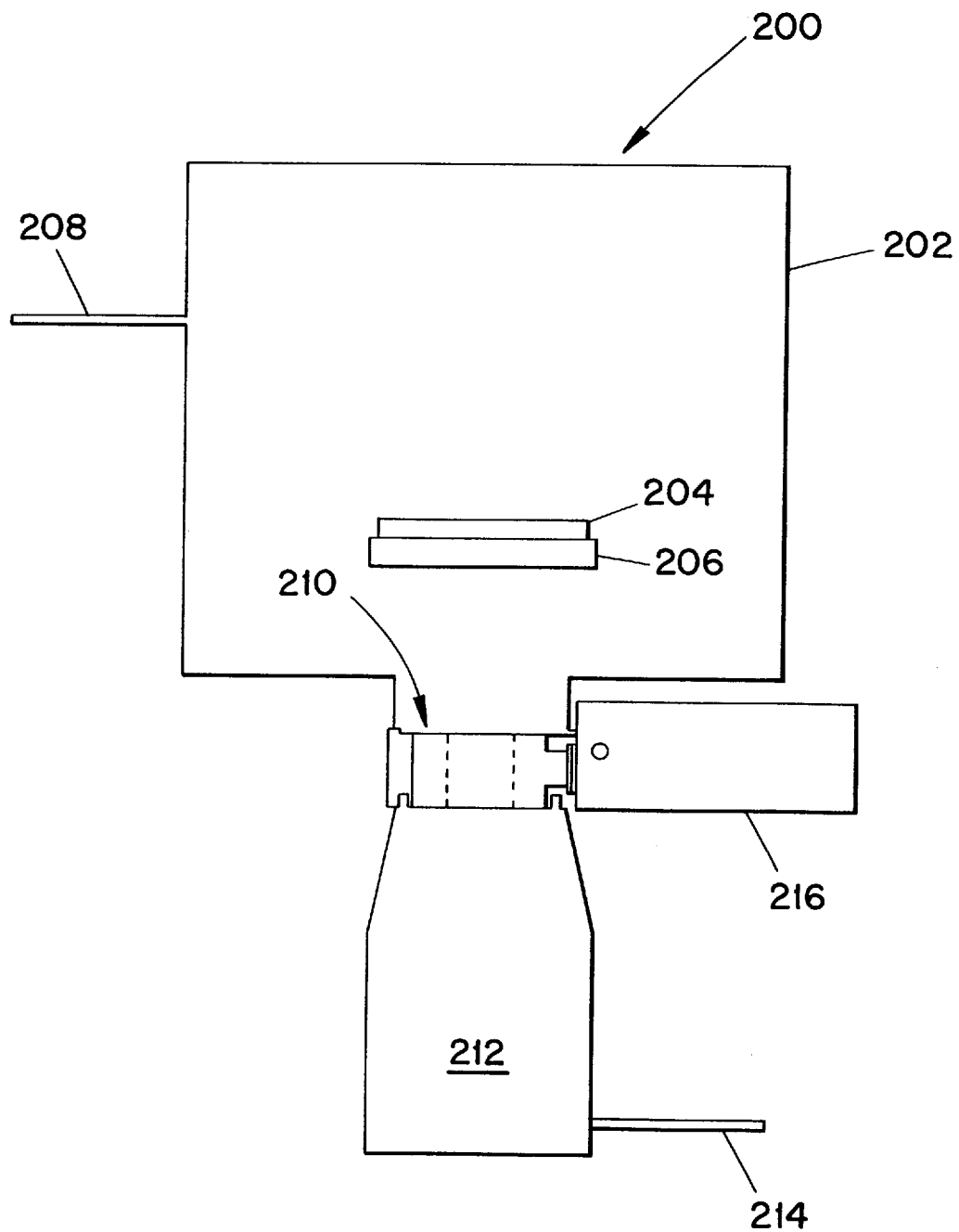
FIG. 2 is a side sectional view of a semiconductor processing apparatus which includes the in-line absorption spectroscopy system of FIG. 1.

With reference to FIG. 2, the spectroscopic sensor system described above allows for in-situ detection of gas phase molecular species in a gas exhausted from a vacuum chamber, wherein the cell can be disposed between a vacuum chamber and a vacuum pump system or be disposed within the vacuum chamber itself. The system is particularly well suited for use in monitoring gas phase molecular species, such as moisture (water vapor), methane, or carbon dioxide in a semiconductor processing apparatus, as real time in-situ monitoring of the process can be realized. Accordingly, the inventive method finds particular applicability in the calibration of such a sensor system.

In the exemplary configuration shown in FIG. 2, semiconductor system 200 includes a vacuum chamber 202 inside which a semiconductor substrate 204 is disposed on a substrate holder 206. One or more gas inlets 208 are provided for delivering a gas or plural gases to the vacuum chamber, which is evacuated through an exhaust opening 210 in the vacuum chamber.

A vacuum pump 212 for evacuating the vacuum chamber is connected thereto either directly or indirectly through a vacuum line. A pump exhaust line 214 can be connected to the pump, which can be connected to another pump or to a gas scrubber (not shown). In the illustrated embodiment, the spectroscopic sensor system 216 is connected to the exhaust line of the tool, such that the exhaust stream passes through the measurement cell.

By use of the inventive calibration method, the introduction of harmful impurities, such as moisture, into the process chamber during calibration can be avoided, while at the same time providing an accurate and simple calibration method.

While the invention has been described in detail with reference to specific embodiments thereof, it will be apparent to persons skilled in the art that various changes and modifications can be made, and equivalents employed, without departing from the scope of the appended claims.

What is claimed is:

1. A method for calibration of a spectroscopic sensor, comprising the steps of:
   (a) providing a spectroscopic system comprising:
      (i) a measurement cell comprising one or more walls which at least partially enclose a sample region, a light entry port and a light exit port being the same port or separate ports, each said port containing a light transmissive window through which a light beam passes along an internal light path inside said measurement cell;
      (ii) an optical chamber which contains a light source for generating the light beam which passes through the light entry port into the cell, and a detector for measuring the light beam exiting the cell through the light exit port, said light beam passing along an external light path inside said optical chamber; and
      (iii) a gas inlet connected to the optical chamber;
   (b) introducing a calibration gas stream into the optical chamber, said calibration gas stream containing a calibrating gas species and a carrier gas, said calibrating gas species being present in said calibration gas stream in a known concentration; and
   (c) performing a spectroscopy measurement of said calibration gas stream.

2. The method according to claim 1, wherein the spectroscopic sensor is an in-situ spectroscopic sensor.

3. The method according to claim 2, wherein the spectroscopy measurement is an absorption spectroscopy measurement.

4. The method according to claim 3, wherein the absorption spectroscopy is tunable diode laser absorption spectroscopy.

5. The method according to claim 1, wherein the cell is disposed between and in communication with a vacuum chamber and a vacuum pump.

6. The method according to claim 1, wherein the vacuum chamber forms a portion of a semiconductor processing apparatus.

7. The method according to claim 1, wherein said calibration gas stream is removed from a gas cylinder.

8. The method according to claim 1, wherein a source of said calibrating gas species is a permeation device.

9. The method according to claim 1, wherein the calibrating gas species is selected from the group consisting of water vapor, methane and carbon dioxide.

* * * * *